(12) United States Patent
Silien et al.

(10) Patent No.: US 9,897,536 B2
(45) Date of Patent: Feb. 20, 2018

(54) DIFFERENTIAL INFRA RED NANOSCOPY SYSTEM AND METHOD

(71) Applicants: University of Limerick, Limerick (IE); Laserspec, Malonne (BE)

(72) Inventors: Christophe Silien, Limerick (IE); Ning Liu, Limerick (IE); Andre Peremans, Malonne (BE); David Symens, Maizeret (BE); Syed A. M. Tofail, Limerick (IE)

(73) Assignee: University of Limerick, Limerick (IE)

( * ) Notice: Subject to any disclaimer, the term of this patent is extended or adjusted under 35 U.S.C. 154(b) by 0 days.

(21) Appl. No.: 14/758,898

(22) PCT Filed: Jan. 6, 2014

(86) PCT No.: PCT/EP2014/050099
§ 371 (c)(1),
(2) Date: Jul. 1, 2015

(87) PCT Pub. No.: WO2014/106657
PCT Pub. Date: Jul. 10, 2014

(65) Prior Publication Data
US 2015/0338337 A1   Nov. 26, 2015

(30) Foreign Application Priority Data

Jan. 4, 2013   (EP) .................................. 13150265

(51) Int. Cl.
*G01N 21/00*   (2006.01)
*G01N 21/25*   (2006.01)
(Continued)

(52) U.S. Cl.
CPC ....... *G01N 21/255* (2013.01); *G02B 21/0072* (2013.01); *G02B 21/0076* (2013.01); *G02B 27/58* (2013.01)

(58) Field of Classification Search
CPC . G01J 3/42; G01J 1/16; G01N 21/534; G01N 21/59; G01N 21/255
(Continued)

(56) References Cited

U.S. PATENT DOCUMENTS

| 4,360,885 A | 11/1982 | Edgar |
| 5,289,407 A | 2/1994 | Strickler et al. |

(Continued)

FOREIGN PATENT DOCUMENTS

| DE | 4416558 A1 | 8/1995 |
| GB | 2477817 A | 8/2011 |

(Continued)

OTHER PUBLICATIONS

Gustafsson, "Nonlinear structured-illumination microscopy: Wide-field fluorescence imaging with theoretically unlimited resolution," PNAS, 102(37):13081-13086, Sep. 13, 2005.
(Continued)

*Primary Examiner* — Tarifur Chowdhury
*Assistant Examiner* — Md M Rahman
(74) *Attorney, Agent, or Firm* — K&L Gates LLP

(57) ABSTRACT

The invention provides a method and system to record the absorption of a sample, said method comprising the steps of providing first and second pulsed beam of light on said sample using one or more light beams, said first and second pulsed beam having different spatial definition; measuring the difference in intensity transmitted through and/or reflected by a sample; and generating an image by scanning the sample while making such measurements. The system and method of the invention can work down to resolution of several 100 of nm, affording thus a large improvement in comparison to synchrotron IR imaging that is the closest technique existing today. The advantage versus scanning probe approach is the absence of physical probe, thus
(Continued)

(a)

(b)

suppressing confinement to surface information and removing uncertainty regarding the working behavior of the probe.

14 Claims, 3 Drawing Sheets

(51) Int. Cl.
 *G02B 21/00* (2006.01)
 *G02B 27/58* (2006.01)
(58) Field of Classification Search
 USPC .......................................................... 356/434
 See application file for complete search history.

(56) References Cited

U.S. PATENT DOCUMENTS

| | | | |
|---|---|---|---|
| 5,731,588 A | 3/1998 | Hell et al. | |
| 6,046,925 A | 4/2000 | Tsien et al. | |
| 2003/0174560 A1 | 9/2003 | Dahmen et al. | |
| 2006/0119934 A1 | 6/2006 | O'Connell et al. | |
| 2007/0109547 A1* | 5/2007 | Jungwirth | G01J 1/02 356/450 |
| 2008/0151226 A1 | 6/2008 | Hecker et al. | |
| 2010/0039629 A1* | 2/2010 | Xalter | G02B 26/0833 355/67 |
| 2010/0075373 A1* | 3/2010 | Hoyt | G01N 1/30 435/40.5 |
| 2010/0238438 A1 | 9/2010 | Frankel | |
| 2011/0205535 A1* | 8/2011 | Soller | A61B 5/14552 356/300 |
| 2011/0215258 A1 | 9/2011 | Kempe et al. | |
| 2012/0097865 A1 | 4/2012 | Lippert | |
| 2012/0105854 A1 | 5/2012 | Borri et al. | |
| 2012/0140231 A1* | 6/2012 | Knox | G01N 21/53 356/442 |
| 2014/0070111 A1* | 3/2014 | Rappaport | G01N 33/227 250/395 |
| 2014/0307249 A1 | 10/2014 | Peremans et al. | |

FOREIGN PATENT DOCUMENTS

| | | |
|---|---|---|
| JP | 01232316 | 9/1989 |
| WO | 2004/090617 A2 | 10/2004 |
| WO | 2007/106069 A2 | 9/2007 |
| WO | 2010/101894 A2 | 9/2010 |
| WO | 2014/005195 A2 | 1/2014 |

OTHER PUBLICATIONS

Lai et al., "Optical determination and magnetic manipulation of a single nitrogen-vacancy color center in diamond nanocrystal," Advances in Natural Sciences Nanoscience and Nanotechnology, 2010, 6 pgs.

Moffitt et al., "Time-gating improves the spatial resolution of STED microscopy," Optics Express, 19(5), 2011, 13 pgs.

Wildanger et al., "A compact STED microscope providing 3D nanoscale resolution," Journal of Microscopy, 236:35-43, 2009.

Wilson et al., "Difference confocal scanning microscopy," Optica Acta, 31(4):453-465, 1984.

International Search Report and the Written Opinion of the International Searching Authority for International Application No. PCT/EP2014/050099, dated Apr. 4, 2014, 2014, 12 pages.

* cited by examiner

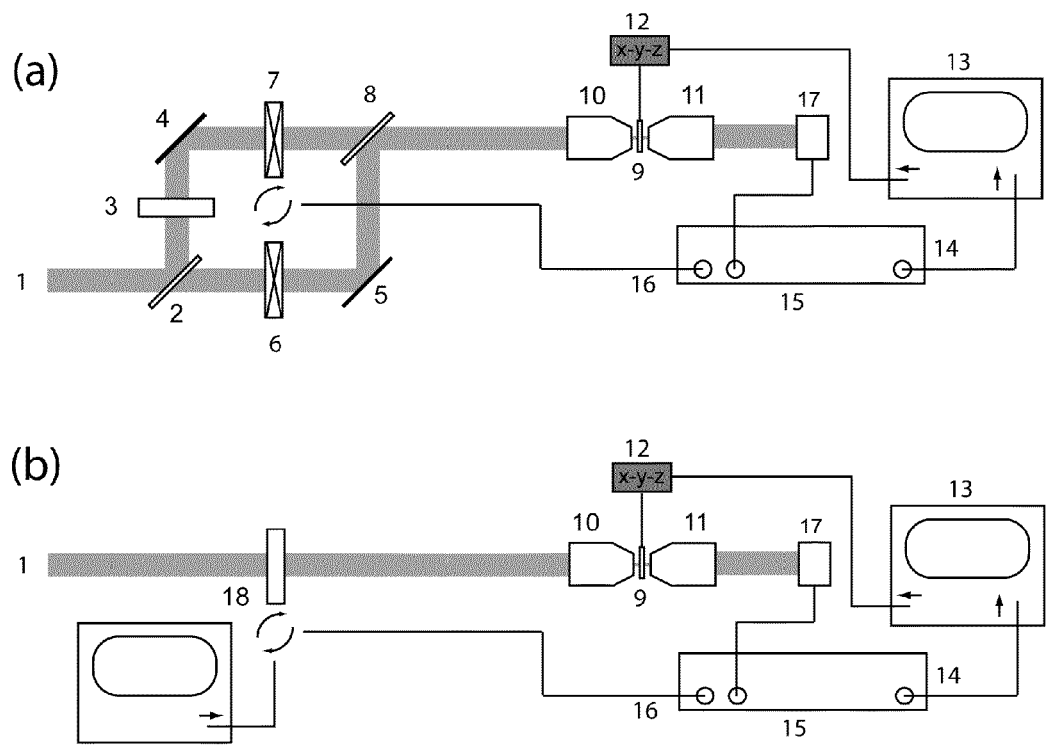
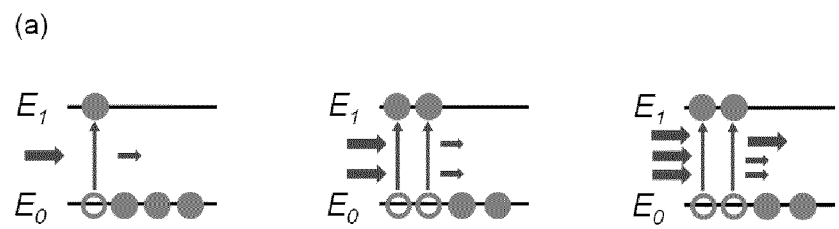
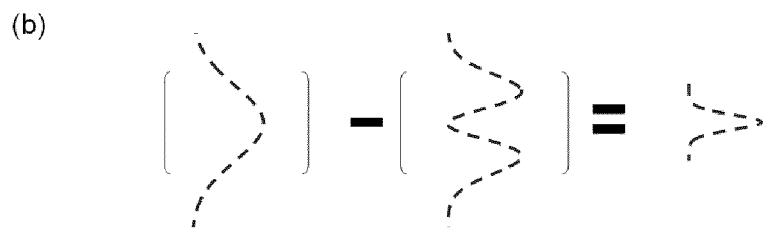
Figure 2

DIFFERENTIAL INFRA RED NANOSCOPY SYSTEM AND METHOD

CROSS REFERENCE TO RELATED APPLICATIONS

This is the national phase under 35 U.S.C. § 371 of International Application No. PCT/EP2014/050099, filed on Jan. 6, 2014, which claims priority to and the benefit of European Patent Application No. 13150265.0, filed on Jan. 4, 2013, the entire disclosures of each of which are incorporated by reference herein.

FIELD

The invention relates to a far-field sub-diffraction imaging system and method.

BACKGROUND

Today it remains difficult to measure the absorbance of samples at high spatial resolution, despite the importance of the infrared, IR (or visible and ultraviolet, UV) absorbance for chemical analysis.

In the far-field, one generally chooses to achieve high resolution chemical imaging by using the shorter wavelength in the visible or near-IR spectrum, typically up to 1 µm wavelength. Indeed the shorter the wavelength the better the resolution, according to the Abbe criterion. One can also use several approaches such as CARS (coherent anti-Stokes spectroscopy) or SRS (stimulated Raman spectroscopy) to obtain chemical imaging. These probe characteristic Raman signature of a sample. A schema for sub-diffraction CARS microscopy has been described in US 2010/0238438 A1 that uses a single pump beam overlapped in time and space into the sample with two interfering 'Stokes' beams of different spatial profile.

IR absorption provides complementary information to Raman spectroscopy and is typically paired with Raman. The obvious advantage of IR absorption is that the cross-section of IR absorption is larger than that of Raman scattering, affording, in principle, a higher sensitivity. The best IR absorption imaging (or IR micro-spectroscopy) is currently carried out using synchrotron IR sources and only affords a diffraction limited resolution (at least several µm).

There is currently no demonstrated far-field methods to improve the resolution of IR absorption imaging up to (or better than) the level of CARS or SRS. To achieve high-spatial resolution when measuring the IR absorbance, one currently needs to exploit near-field probing methods. These are realized by scanning a nanoscale probe in the vicinity of the sample. Resolutions down to several tens of nm (but typically 100-150 nm) have been demonstrated. By nature these techniques are suited to probe the surface of samples, which limit the field of applications. Other publications in the field include patent publication number GB2477817. Furthermore there are inherent difficulties in obtaining probes that effectively work.

Current far-field sub-diffraction microscopies can use the RESOLFT (REversible Saturable OpticaL Fluorescence Transitions) and localization methods (e.g., STORM, PALM, etc). These methods measure the fluorescence of fluorescent molecules that are (in all except very few specific cases) added to samples. These fluorescent molecules are known as chromophores or more generally as 'labels'. DE4416558 and US 2011/0215258 A1 describe implementation of RESOLFT approach. They are thus not suitable for label-free chemical imaging.

Saturated structured-illumination microscopy (SSIM) has been proposed by Gustafson (M. G. L. Gustafsson, Proc. Natl. Acad. Sci. U.S.A. 2005, Vol. 102, 13081-13086). However SSIM is also realized in the case of fluorescent molecule and is not designed to record the IR absorbance (nor the visible/UV one). SSIM uses a complex image processing and is a wide-field approach. A similar schema using a selectively directed, focused illumination beam and a wide field array detector has been proposed in PCT patent publication number WO2010/101894 A2.

Moreover, a paper published by Wilson et al (T. Wilson and D. K. Hamilton, Optica Acta 1984, Vol. 31, 453-465) describes a schema where a single point source of light, in its virgin state i.e. without any modification, goes on a sample that is being scanned for imaging. The resultant beam from the sample is then split into two beams and the differential signal is established as the difference in intensity measured by two different detectors, a confocal detector and a large area detector.

US2012/0097865 describes a differential scheme of improving resolution of visible imaging based on luminescence (fluorescence and similar effects) and requires the addition of 'labels'. In this technique the luminescence emitted from the labels in the sample is measured at sub-diffraction resolution by using two beams, partially but not completely overlapping on the sample, to excite the luminescence. Other publications in the field include patent publication numbers WO2007106069 and US2006119934.

It is an object of the invention to provide a method and system based on a measure of the absorption of light (IR, visible or UV) by a sample for its sub-diffraction imaging in the far-field.

SUMMARY OF THE INVENTION

According to the invention there is provided, as set out in the appended claims, a method to record the light absorption of a sample, said method comprising the steps of:
  providing first and second pulsed beams of light on said sample using one or more light beams, said first and second pulsed beams having different spatial definition;
  measuring the difference in intensity for said first and second pulsed beams transmitted through and/or reflected by a sample; and
  generating an image of the sample from said measured difference in intensity.

The system and method of the invention can achieve a resolution of several hundreds of nm, affording thus a large improvement in comparison to synchrotron IR absorption imaging that is the closest comparable technique existing today. The advantage of the invention over scanning probe approach is the absence of a physical probe, thus suppressing the confinement to surface information and removing uncertainty regarding the working behaviour of the probe. Compared to SRS and other Raman-based approach, the invention affords the complementary IR signature but also measure a more sensitive quantity, having thus more sensitivity. The system and method of the invention removes the need for timely controlled pumping of the samples making the realization much simpler than any RESOLFT-based approach.

In one embodiment there is provided the step of recording the variation in the intensity of the pulsed beams transmitted through and/or reflected by the sample by synchronous detection.

In one embodiment the measuring step measures vibrational information of the sample.

In one embodiment one light beam is adapted to provide a first and a second pulsed light beams, wherein the beams comprise a different spatial definition.

In one embodiment the first and second pulsed light beams are selected at intensities to saturate the absorption of the sample, such that the level of saturation provides sub-diffraction resolution.

In one embodiment there is provided the step of comparing intensity of the transmitted and/or reflected first and second beam of light, wherein said beams are adapted to be co-aligned and comprising a different spatial definition.

In one embodiment there is provided the step of shaping or modulating a point-spread function into a point-like shape to generate the said image.

In one embodiment no chemical nor structural properties of the sample are modified for the measurement steps.

In another embodiment there is provided a method to record the absorption of a sample, said method comprising the steps of:
  providing first and second pulsed beam of light on the said sample using one or more light beams, wherein said first and second pulsed beam have different spatial definition;
  measuring the difference in intensity for both first and second pulsed beams transmitted through and/or reflected by the sample; and
  generating an image by scanning the sample while making such measurements.

In a further embodiment of the invention there is provided a system to record the absorption of a sample, said system comprising:
  means for providing first and second pulsed beam of light on the said sample using one or more light beams, wherein said first and second pulsed beam have different spatial definition;
  means for measuring the difference in intensity for both first and second pulsed beams transmitted through and/or reflected by the sample; and
  means for generating an image by scanning the sample while making such measurements.

In another embodiment there is provided system to record the light absorption of a sample, said system comprising
  means for providing first and second pulsed beams of light on said sample using one or more light beams, said first and second pulsed beams having different spatial definition;
  means for measuring the difference in intensity for said first and second pulsed beams transmitted through and/or reflected by a sample; and
  means for generating an image of the sample from said measured difference in intensity.

In one embodiment there is provided means for recording by synchronous detection the variation in intensity of the pulsed beams transmitted and/or reflected through the sample.

In one embodiment the synchronous detection comprises a lock-in amplifier.

In one embodiment the synchronous detection approach comprises making measurements of the intensity of alternating first and second pulsed beams having different spatial definition.

In one embodiment the measuring means measures the IR absorbance of the sample.

In one embodiment the absorption of the sample is measured in the UV-visible wavelength range (measuring the UV-vis absorption of the sample).

In one embodiment one light beam is adapted to provide a first and a second pulsed beam wherein the pulsed beams comprise a different spatial definition.

In one embodiment there is provided means for comparing the intensity of transmitted or reflected first and second beam of light, the said beams are adapted to be co-aligned and comprising a different spatial definition.

In one embodiment the first pulsed light beam comprises a zeroth order Gaussian beam.

In one embodiment the second pulsed light beam comprises a Gaussian beam of higher order than the first light beam (also called vortex beam, exhibiting a central node).

In one embodiment there is provided means for shaping a point-spread function into a point-like shape to generate said image.

In one embodiment no chemical nor structural properties of the sample are modified for the measurement means.

There is also provided a computer program comprising program instructions for causing a computer program to carry out the above method which may be embodied on a record medium, carrier signal or read-only memory.

BRIEF DESCRIPTION OF THE DRAWINGS

The invention will be more clearly understood from the following description of an embodiment thereof, given by way of example only, with reference to the accompanying drawings, in which:

FIGS. 1(a) and (b) illustrate two basic configurations of the system according to first and second embodiments of the invention;

FIG. 2(a) illustrates that a beam of photons passing through the sample will excite some oscillators and (b) that sub-diffraction resolution can be achieved by modifying periodically in time the shape of the beam;

DETAILED DESCRIPTION OF THE DRAWINGS

Figure 3:
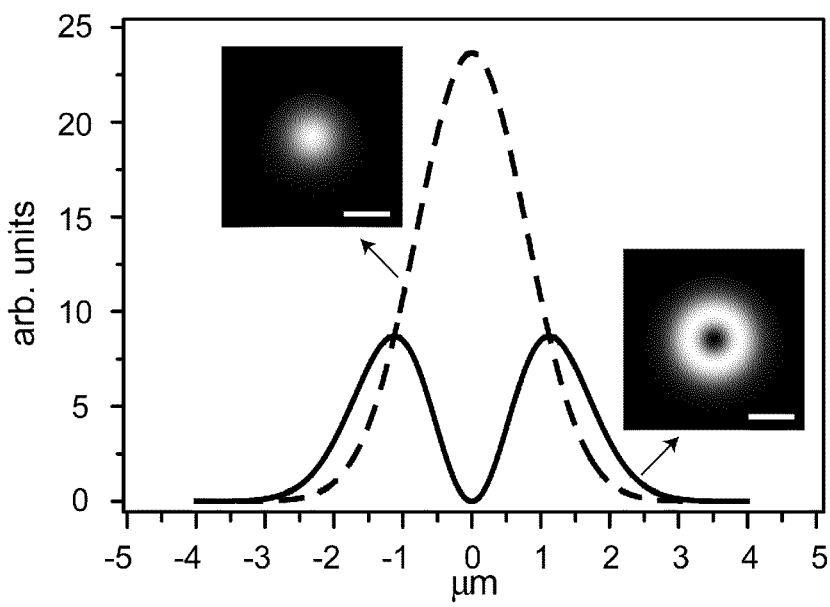
FIG. 3 illustrates a radial profile of the two beams as used in one embodiment.

The invention provides a method and system to record the infrared absorption of samples with a spatial resolution below the diffraction limit. The method will work in the same way for infrared (mid- and near-), visible and UV absorption. The procedure described here is for a transmission geometry but reflection geometry is also possible. The procedure is described in the case of 2D imaging and the procedure can be extended to 3D imaging. The infrared absorption spectra allow identifying and locating the vibrational modes that are present in materials. These modes occur at IR frequencies that are characteristics of the sample and thus recording the IR absorption is a way to measure chemical information from samples. When images of the absorption are produced, one refers to them as chemical images.

FIG. 1(a) illustrates an example configuration according to one embodiment of the invention method to record the absorption of a sample. A light source (1), for example a laser source (not represented), provides a light beam that can be split in two by a beam splitter (2) to generate the two beams and one path will be going through a phase filter to shape the Gaussian beam into a doughnut using an helicoidal phase plate (3) (if one choose to work with Gaussian and doughnut signal). The beam path can be controlled by mirrors (4, 5). Choppers (6, 7) allow for using either one beam or the other (i.e. the two choppers are out-of-phase in this embodiment). Beams are co-aligned using a beam splitter (8). It will be appreciated that the two pulsed beams can be provided by a single light beam where the spatial definition of the beam is repeatedly varied. The sample (9) is positioned between two objectives (10, 11) and adapted to be scanned by a scanner (12). A computer (13) controls the scanner and records a differential signal (14) generated by a lockin amplifier (15), which is locked onto a reference signal (16) in tune with the choppers (6,7) and which measures the signal issued by a photodetector (17). It will be appreciated that other components can be used to provide the beams of light and measure the intensity. The system measures the difference in transmitted intensity (but reflected intensity is possible by adding a beam splitter before the sample and placing the detector at the output of that beam splitter); and generates an image by scanning the sample when making such measurements.

FIG. 1(b) illustrates a variation of the embodiment where a computer controlled wavefront modulator (18) is used. The wavefront modulator provides the means for providing first and second pulsed beams of light on the sample. The operation of the embodiment shown in FIG. 1(b) is similar to herein described with respect to FIG. 1(a) and can provide for easier beam alignment.

In operation, a sample is prepared similar as for synchrotron IR imaging or for IR microscope based on Globar sources. Working in reflection geometry or transmission geometry is also possible. The sample is placed between the two objectives of the microscope (a confocal configuration will afford ultimately a better resolution and is thus preferred, although not indispensable). The procedure is to focalize, in alternance, a beam of Gaussian shape and a beam of doughnut shape (other beam shapes are however possible) and to record the subsequent variation in intensity transmitted through the sample. This can be done simply by synchronous detection (for example with a lock-in amplifier) on the intensity using a reference signal in tune with the frequency of alternance of the beams. Shutters can be used to block one beam while the other passes and vice versa, creating the alternance (other shutter configurations/technologies are possible). Note that the precise shape of the two beams does not matter as long as one exhibits one node where the other one does not. It can be shown that the signal, here the output of the lockin amplifier, allows generating imaging at sub-diffraction resolution.

The systems of FIG. 1 use a scanning technique and the measure is repeated by varying the position of the sample in the beams. For simplicity both beams are centered and focalized at same position. However, there are some restrictions on the configuration (essentially one node should face an anti-node). High spatial resolution is achieved because the non-linearity of the absorbance.

FIG. 2(a), it is explained that considering a relaxed sample of oscillators, a beam of photons passing through the sample will excite some oscillators. There is a probability for this to happen, that is the base of the IR absorption spectroscopy or microspectroscopy. Some photons are thus lost and measuring the ratio of the intensity before and after transmission through the sample gives the absorbance (strictly speaking, by definition of the absorbance, one should further compute the logarithm of this ratio). From left to right, what is seen is that increasing the incident photon flux (i.e., beam intensity) does lead first to an increase in lost photons (i.e., absorption), and at later stage when saturation is achieved (i.e., for a two level system this happens when the population of the fundamental and excited states are equal) the number of absorbed photons remains the same. The saturation is the origin of the sub-diffraction resolution.

In FIG. 2(b), it is illustrated that the sub-diffraction resolution can be achieved by modifying periodically in time the shape of the beam (e.g., between a Gaussian and a doughnut) and by recording the difference of transmitted IR light. The variation of transmitted and/or reflected light in tune with the beam shape variation is what the lockin amplifier will measure. Lockin amplification is a method well used in physics and is also called synchronous detection.

Results are shown to illustrate one possible point-spread-function (PSF), that represents the image of a point (in theory of a Dirac function, simulated here by a sample active in a single pixel only ($25 \times 25$ nm$^2$)). All beams are of circular geometry, so only the radial coordinate is represented. The full-width at half-maximum (fwhm) of the PSF is taken as the resolution, as is usually done. The simulation is the result of the solution of the following system of equation (both are well known from undergraduate optics textbooks):

$$\frac{dN}{dt} = -\Gamma N(z, t) - \beta \Delta N(z, t) I(z, t)$$

$$\text{and } \frac{\partial I}{\partial z} = h\nu \beta \rho \Delta N(z, t) I(z, t),$$

where $\Gamma$ is the rate of spontaneous de-excitation, $\beta$ is the stimulated emission/absorption Einstein coefficient normalized to the speed of light, $\Delta N$ is the difference in relative population density between the two levels, N is the population density of the excited state, I the local intensity (encompassing only the photons that can be absorbed by the oscillators), z the position along the direction of propagation, and t the time. hv is the photon energy and $\rho$ the density of oscillators.

The sample is thus described by $\rho$, $\beta$, and $\Gamma$, whose values can be made dependent on all three dimensions of space. A Mathlab code can be written to solve the system of equations, developed using the backward Euler approach and leaving N, $\Delta N$, and I to also depend on the coordinates in the sample plane normal to z. The solution of the system is readily found by iteration by realizing that N $(z,t_0)=0$, because virtually only the fundamental state is occupied at room temperature, and that I $(z_0,t)$ corresponds to the temporal evolution of the intensity impinging the sample. The energy of the outgoing probe pulse $\Sigma$ is obtained by integrating over the duration of one pulse where the coordinate z exceeds the sample depth, and over the sample plane normal to z. IR absorption images and sub-diffraction images are computed by repeating the process varying the relative position of the pulses with respect to the sample. The Differential InfraRed Nanoscopy (DIRN) signal is defined as:

$$DIRN(\%) = \frac{\sum_{dnut}(z) - \sum_{gss}(z)}{\sum_{gss}(z_0)} \times 100,$$

where $\Sigma_{gss}(z_0)$ is the Gaussian probe pulse computed at the entrance of the sample in $z_0$ (or in the absence of sample), $\Sigma_{dnut}(z)$ is the transmitted signal for a doughnut-shape beam and $\Sigma_{gss}(z)$ is the transmitted signal for a Gaussian-shape beam. Note that using doughnut (i.e., first order Gaussian) and Gaussian (i.e., zeroth order Gaussian) beams are the most obvious embodiment but are not the sole solution. The signal measured experimentally can be:

$$DIRN = A(\Sigma_{dnut}(z) - \Sigma_{gss}(z))$$

where A is a constant of calibration. Referring to the percentage as done above is useful here since it provides an estimation of the signal contrast and can thus be used to assess the difficulty of recording experimentally the signal. But experimentally if a reference signal is measured it is also possible to record the DIRN (%) as well.

To simulate the point-spread function (PSF) of the DIRN microscopy, a sample was defined in a single pixel of $25 \times 25$ nm$^2$ using probes defined by:

$$\varepsilon_0(r, \theta) = \sqrt{\frac{2}{\pi}} \, e^{-r^2/w_0^2}$$

$$\text{and } \varepsilon_1(r, \theta) = \sqrt{\frac{2}{\pi}} \, \frac{\sqrt{2}r}{w_0} e^{-r^2/w_0^2} e^{i\theta}$$

The first correspond to a Gaussian profile and the second to the doughnut profiles. The beams are normalized to achieve energies of 1 nJ, 10 nJ, 100 nJ and 1 µJ. The waist $w_0$ is chosen 1.59 µm for the doughnut and 1.2 times larger for the Gaussian (those values are experimentally reasonable for high NA optics, when working at 3.5 µm which is the resonance wavelength of C-H stretch modes). Again this is a suitable geometry used here, but not mandatory for the concept or its practical realization. The probes are set as pulses of 1 ps Gaussian fwhm in the time domain. From a practical point of view other durations can be used, as long as the peak intensity can be reached.

FIG. 3 shows the radial profile of the two beams as used in one embodiment. Both are presented here for a pulse energy of 1 nJ and 1 ps fwhm in the time domain. The experimental value of 0.5% absorption for a uniform octadecylsilane monolayer is reproduced by setting β at 1.4 nm$^2 \cdot$fJ$^{-1}$ and the density of oscillators ρ at 31.5 nm$^{-3}$, which accounts for a thickness of 2.0 nm, an area of 27 Å$^2$ per molecule (alkane self-assembled monolayer), and 17 oscillators (CH$_2$ moieties) per molecule. Γ is set to the averaged experimental value of 0.1 ps$^{-1}$ (corresponding to a lifetime of 10 ps). However, the value of Γ is not very critical for DIRN. Thus it is possible to compute the DIRN image in transmission of a square domain of octadecylsilane $25 \times 25$ nm$^2$ on a transparent substrate, in order to simulate the PSF of DIRN microscopy.

Figure 4:
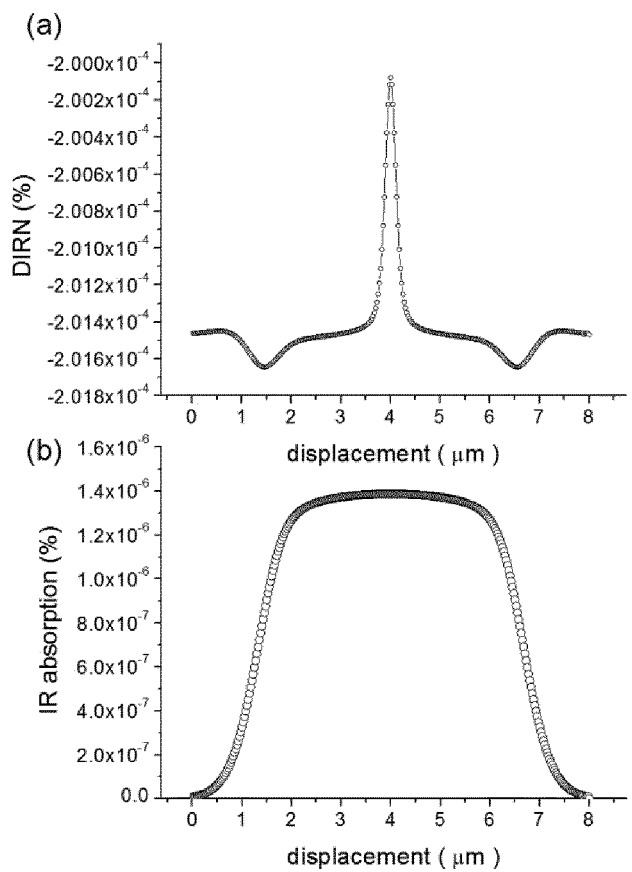
FIG. 4(a) shows the computed DIRN PSF according to one embodiment and (b) the computed traditional IR absorption PSF for comparison.

FIG. 4(a) shows the computed DIRN PSF according to one embodiment and FIG. 4(b) the traditional IR PSF for comparison. One sees that for DIRN the peak fwhm is ca. 275 nm for 100 nJ. One also sees negative signals away from the peak, the precise shape of these structures are dependent on the details of the probe beam shapes. One can optimize the beam shape to minimize those effects or use de-convolution of the images to suppress the artifact. This would be a straightforward de-convolution however and would not require complicated algorithm as in the case of SSIM (Gustafson's method).

Figure 5:
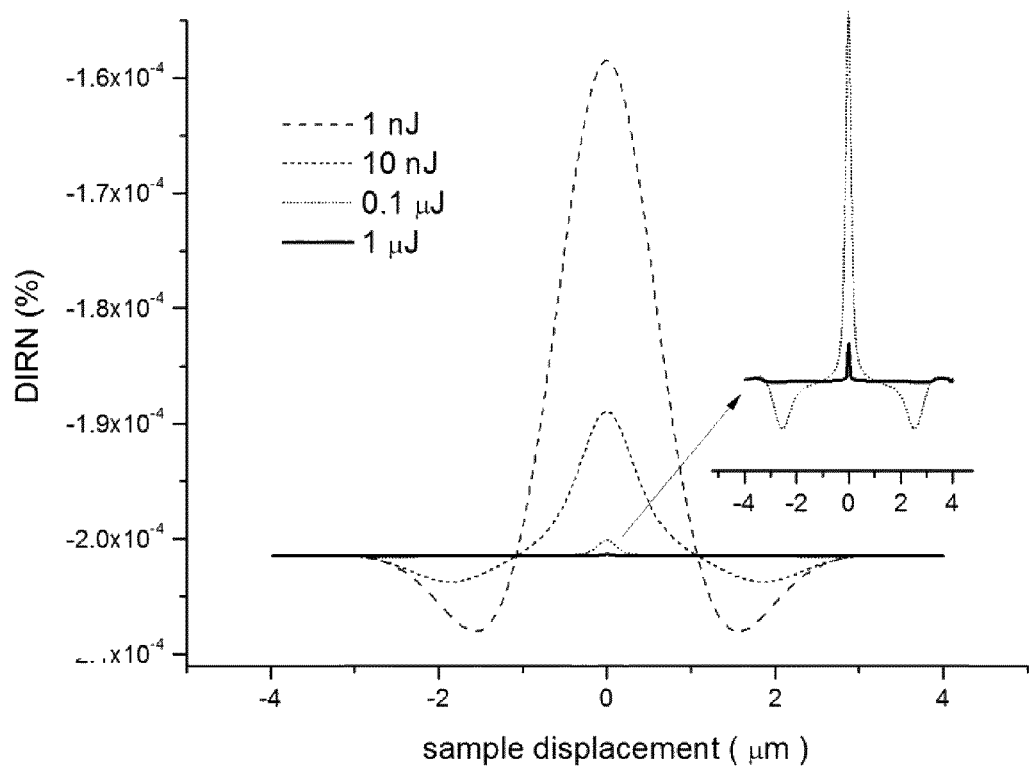
FIG. 5 illustrates the computed DIRN PSF for different pulse energy.
Figure 6:
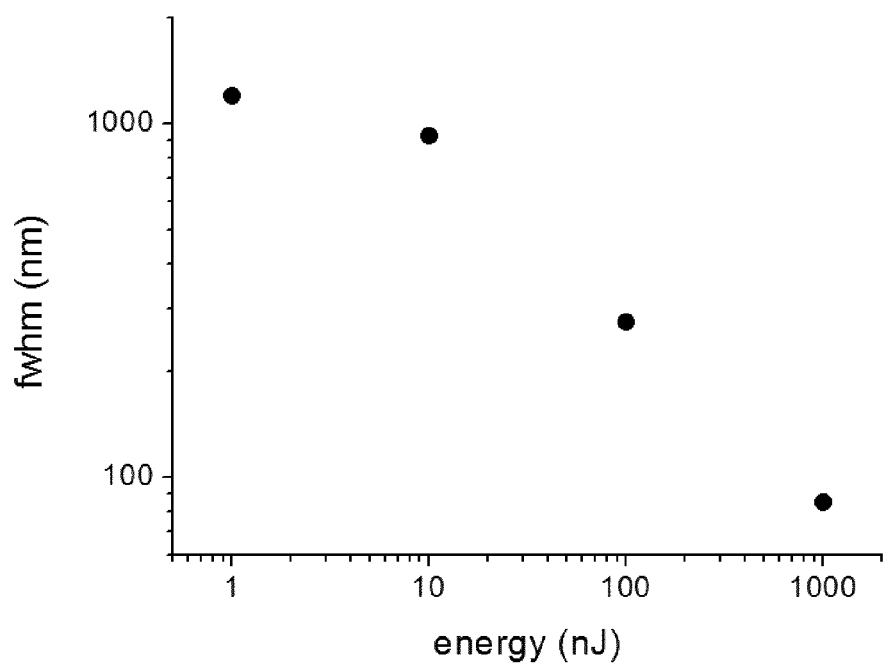
FIG. 6 illustrates the FWHM (full-width at half maximum) of the DIRN PSF central peak for different pulse energy.

FIG. 5 shows the computed PSF for energies of probe 1 nJ, 10 nJ, 100 nJ and 1 µJ. One sees that the resolution is improved below 100 nm for 1 µJ (also see inset) and that the % of signal contrast decreases with increasing probe energies. The quality of the synchronous detection will be thus limiting the resolution. The present invention is nonetheless suitable for sub-diffraction imaging, a priori down to 100 nm. Monolayer thick $250 \times 250$ nm$^2$ pixel will give a signal contrast of ca. $10^{-6}$ smaller than the intensity at the photodetector for a resolution of 250 nm (thicker sample will involve larger signal contrasts). Thus, although the quality of the lockin and the noise level will limit the signal/resolution, nanoscale imaging is possible since near-field measures with ratio of $10^{-8}$ have been demonstrated. Note that the resolution is also sub-diffraction (1.3 µm) even for 1 nJ, which is below the saturation threshold, as shown in FIG. 5 and FIG. 6.

It will be appreciated that the sub-diffraction resolution is achieved by synchronously detection of the variation of intensity transmitted through the sample. The method can work for IR in transmission as illustrated here, on the basis of a regular IR microscope (also confocal). The absorbance is measured so that the principle also holds for shorter wavelengths, including thus the visible and UV ones. Imaging non-transparent samples is possible in reflection geometry, which the procedure equally allows.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:
1. A method to record light absorption of a sample, said method comprising the steps of:
    providing first and second pulsed beams of light on said sample using one or more light beams, said first and second pulsed beams having a different beam shape such that one light beam exhibits a node where the other light beam does not;

measuring the difference in intensity for said first and second pulsed beams transmitted through and/or reflected by the sample; and generating an image of the sample from said measured difference in intensity;

wherein the first light beam comprises a zeroth order Gaussian focalized on the sample, wherein said first and second beams are adapted to be co-aligned, and wherein the first and second light pulsed beams are selected at an intensity to achieve saturation, such that the level of saturation provides sub-diffraction resolution.

2. The method of claim 1 comprising the step of recording variation in intensity transmitted through and/or reflected by the sample by synchronous detection.

3. The method of claim 1 comprising the step of recording variation in intensity transmitted through and/or reflected by the sample by synchronous detection wherein the synchronous detection comprises a lock-in amplifier.

4. The method of claim 3 wherein the synchronous detection approach comprises making measurements of the alternate first and second pulsed beams.

5. The method of claim 1 wherein the absorption of the sample is measured in the Infrared wavelength range.

6. The method of claim 1 wherein the absorption of the sample is measured in the UV, visible, or near-infrared wavelength range.

7. The method of claim 1 comprising one light beam adapted to provide a first and second pulsed beam.

8. The method of claim 1 comprising the step of shaping a point-spread function into a point-like shape to generate said image.

9. The method of claim 1 wherein no chemical nor structural properties of the sample are modified for the measurement.

10. A system to record light absorption of a sample, said system comprising:

a light source for providing first and second pulsed beams of light on said sample using one or more light beams, wherein said first and second light pulsed beams are selected to have an intensity to achieve saturation, such that the level of saturation provides sub-diffraction resolution, wherein said beams are adapted to be co-aligned, wherein said first and second pulsed beams having a different beam shape such that one light beam exhibits a node where the other light beam does not, and wherein said first light beam comprises a zeroth order Gaussian focalized on the sample;

a synchronous detection module for measuring the difference in intensity for said first and second pulsed beams transmitted through and/or reflected by the sample; and a computer for generating an image of the sample from said measured difference in intensity.

11. The system of claim 10 comprising a synchronous detection module for measuring the difference, wherein the synchronous detection comprises a lock-in amplifier.

12. The system of claim 10 wherein the absorption of the sample is to be measured in the Infrared wavelength range.

13. The system of claim 10 wherein the absorption of the sample is measured in the UV, visible, or near-infrared wavelength range.

14. The system of claim 10 comprising one light beam adapted to provide a first and second pulsed beam.

* * * * *